United States Patent [19]

Kasprzak

[11] 4,324,595
[45] Apr. 13, 1982

[54] METHOD FOR REMOVING TACKY ADHESIVES AND ARTICLES ADHERED THEREWITH

[75] Inventor: Kenneth A. Kasprzak, Saginaw, Mich.

[73] Assignee: Dow Corning Corporation, Midland, Mich.

[21] Appl. No.: 71,453

[22] Filed: Aug. 31, 1979

[51] Int. Cl.³ .............................................. B08B 3/08
[52] U.S. Cl. ...................................... 134/38; 134/42; 424/184
[58] Field of Search .................. 134/38, 42; 156/344; 252/174.15; 424/184

[56] References Cited

U.S. PATENT DOCUMENTS

| | | | |
|---|---|---|---|
| 2,221,960 | 11/1940 | Abramowitz | 156/344 X |
| 2,500,107 | 3/1950 | Weichselbaum | 156/344 X |
| 3,000,773 | 9/1961 | Shapiro | 156/344 |
| 3,071,498 | 1/1963 | Kaskel | 252/174.15 X |
| 3,789,118 | 1/1974 | Broerman | 424/184 X |
| 3,920,472 | 11/1975 | Vinson | 134/38 X |
| 3,998,654 | 12/1976 | Falaas et al. | 134/38 X |

OTHER PUBLICATIONS

Dow Corning, "Information About Silicone Fluids", 1978.

Primary Examiner—Marc L. Caroff
Attorney, Agent, or Firm—George A. Grindahl

[57] ABSTRACT

Tacky adhesives are removed from a substrate by a non-stinging, non-drying, non-staining, non-solvent process. The process uses a volatile methylsiloxane fluid to detackify the adhered adhesive, after which it is easily removed. This process is particularly useful for removing tacky adhesives from the human skin. A highly preferred volatile methylpolysiloxane fluid is octamethylcyclotetrasiloxane.

5 Claims, No Drawings

METHOD FOR REMOVING TACKY ADHESIVES AND ARTICLES ADHERED THEREWITH

BACKGROUND OF THE INVENTION

The present invention relates to a method for removing a tacky adhesive from a substrate. In particular, this invention relates to a method for removing a tacky medical adhesive from the human skin.

Tacky adhesives are widely used today. For example, articles, such as labels, decals, decorative trim, medical devices and bandages are routinely adhered to a substrate with a pressure-sensitive tacky adhesive.

When it becomes desirable to remove an adhered article, and its tacky adhesive, from a substrate a solvent for the adhesive is usually used. However, this use of a solvent is frequently undesirable. For example, a solvent for the tacky adhesive may damage the substrate. In addition many solvents have an unpleasant odor and/or a toxic effect and/or an irritating action. These shortcomings of solvents are particularly important when the substrate is the human skin.

Many medical articles, such as colostomy, ileostomy and ureterostomy devices, must be repeatedly adhered to and removed from the patient's skin. A non-irritating, non-drying, non-toxic method of removing such devices, and any residual adhesive, is highly desirable.

Other medical articles, such as bandages and electrodes, although not frequently adhered, are adhered to areas of the human skin which are frequently lacerated, abraded or otherwise made sensitive. A non-stinging method of removing articles, and any residual adhesive, from sensitive skin, is highly desirable.

It is known to mix a small amount of a non-volatile silicone fluid with a solvent for the adhesive to mitigate the irritating and/or drying effect that the solvent has on the human skin when used to remove tacky adhesives. However, such a composition still has a stinging effect on sensitive skin.

SUMMARY OF THE INVENTION

It is an object of this invention to provide an improved method for removing a tacky adhesive from the human skin.

It is another object of this invention to provide a substantially non-solvent method for removing a tacky adhesive from a substrate.

It is a further object of this invention to provide a non-staining, non-stinging, non-drying, non-toxic method for removing a tacky adhesive from the human skin.

It is also an object of this invention to provide an improved method of removing an article which has been adhered to a substrate with a tacky adhesive.

These objects, and others, are achieved by applying a volatile methylsiloxane fluid to a tacky adhesive which is adhered to a substrate. The adhesive is readily detackified and is easily removed, along with any article adhered therewith, from the substrate by this method. A minimum amount of rubbing is needed to remove the detackified adhesive, thereby minimizing damage to the substrate. The volatile methylsiloxane fluid is non-stinging, non-toxic and non-irritating to humans and does not stain clothing.

DETAILED DESCRIPTION OF THE INVENTION

The present invention relates to a process for removing a tacky adhesive from a substrate, said process comprising applying a volatile methylsiloxane fluid to said tacky adhesive and removing the thus-treated tacky adhesive from said substrate.

The present invention further relates to a process for removing an article from a substrate, adhered thereto with a tacky adhesive, said process comprising applying a volatile methylsiloxane fluid to said tacky adhesive and removing said article and its tacky adhesive from said substrate.

Volatile methylsiloxane fluids which are operable in the method of this invention leave substantially no residue after 30 minutes at room temperature when 1 gram thereof is placed at the center of a No. 1 circular filter paper having a diameter of 185 mm. and being supported by its perimeter in the open room atmosphere.

By methylsiloxane it is meant a composition containing two or more silicon atoms, all of which are bonded by way of at least one oxygen atom to at least one other silicon atom, and at least one methyl radical, each silicon valence not satisfied by oxygen being satisfied by a methyl radical. Thus a methylsiloxane consists of two or more of the siloxane units having the formulae $Me_3SiO_{1/2}$, $Me_2SiO_{2/2}$, $MeSiO_{3/2}$ and $SiO_{4/2}$, wherein Me denotes the methyl radical.

Preferred volatile methylsiloxane fluids for the method of this invention include $Me_3SiOSiMe_3$ (b.p.=99.5° C.), $Me_3SiOMe_2SiOSiMe_3$ (b.p=152° C.), $(Me_2SiO)_3$ (b.p.=133° C.) and $(Me_2SiO)_4$ (b.p.=171° C.), i.e. hexamethyldisiloxane, octamethyltrisiloxane, hexamethylcyclotrisiloxane and octamethylcyclotetrasiloxane, respectively, and any mixture of any two, three or all of said preferred fluids. The normal boiling point of each fluid is noted parenthetically after each formula.

A volatile methylsiloxane fluid having a particular evaporating behavior, different from any one fluid, can be prepared by mixing two or more volatile methylsiloxane fluids, having different volatilities, in the proper proportions in the well-known manner.

Methylsiloxane fluids are well known; many are commercially available. Their synthesis is well documented in the polymer literature and needs no further elaboration herein. Hexamethyldisiloxane and octamethylcyclotetrasiloxane find use in cosmetic and personal care formulations such as antiperspirants, deodorants, hair sprays, hair grooming aids, skin creams, lotions and stick products.

Tacky adhesives that are removed from a substrate by the process of this invention are of the type that operate by retaining their tackiness and do not operate by becoming hard during use. They are frequently called pressure-sensitive adhesives and possess a wide range of strengths, varying from engineering or structural strength materials to weak, jelly-like materials. Tacky adhesives possess measurable adhesion and tack. Adhesion is measured by ASTM D1000-78. Tack is ASTM D2979-71.

Examples of tacky adhesives that are removed by the method of this invention include adhesive-bandage adhesive, surgical-tape adhesive, adhesive-tape adhesive, pressure-sensitive-label adhesive and stress-electrocardiogram-electrode adhesive.

It is to be understood that the process of this invention extends to the removal of an object adhered to a substrate as well as to the removal of the adhesive, or any residual portion thereof, from the substrate.

Thus, it is within the scope of the present invention to apply a volatile methylsiloxane fluid to a porous article such as a paper label or an adhesive tape which has been adhered to a substrate and to allow the fluid to penetrate the article to be removed and detackify the underlying adhesive. The article and its adhesive are readily removed.

Furthermore, a volatile methylsiloxane fluid may be applied to the substrate of an adhesive-bearing substrate, adjacent to the adhesive to be removed, and allowed to permeate and detackify the adhesive from the perimeter of the adhesive.

It is also within the scope of this invention to apply a volatile methylsiloxane fluid to a porous substrate and allow the fluid to penetrate the substrate to reach and detackify an adhered adhesive.

In the process of this invention force may be used to apply the volatile methylsiloxane fluid and/or to remove the detackified adhesive, if desired. For example, a gentle brushing motion on a skin bandage with a cotton swab or ball containing the volatile methylsiloxane fluid may be desired.

Although the process of this invention has particular application in the human health field for removing tacky adhesives from the skin and hair and in veterinarian science for the removal of tacky adhesives from the skin, fur, hair, feathers, etc. of other animals, the nature of the substrate bearing the adhesive and/or adhered article to be removed is not critical. The process of this invention is applicable to any substrates, such as metal substrates such as steel, iron, stainless steel, copper, aluminum, silver and gold; siliceous substrates such as glass and brick; painted substrates; textiles, such as cotton, polyester, nylon, wool and rayon; rubber; wood; polyethylene and other plastics such as urea-formaldehyde and phenol-formaldehyde resins, fiberglass and plexiglass.

The process of this invention comprises the mixing of non-deleterious components with the volatile methylsiloxane fluid, if desired, such as effacacious ingredients such as non-volatile silicone fluids, medicaments, cleansing agents and substrate-protecting components and other non-deleterious components such as colorants, odorants and propellants.

The volatile methylsiloxane fluid may be applied in any suitable manner such as by spraying, pouring, vapor depositing, syringing, dropping, rubbing, dabbing, squirting, soaking, immersing and misting.

A particular advantage of the process of this invention is the non-stinging, non-irritating, non-staining, non-solvent benefits that are obtained from the use of the volatile methylsiloxane fluid, free of any additional components, to remove a tacky adhesive from a wide variety of substrates.

To further delineate, but not to limit, the present invention the following examples are disclosed.

EXAMPLE 1

In preparation for a stress-electrocardiogram the upper layers of skin of a patient's chest and limbs were rubbed away with a cleansing gauze and electrodes were adhered to the prepared areas using a tacky medical adhesive. Following the stress-electrocardiogram the electrodes were pulled from the patient's skin and alcohol was used to remove some residual adhesive. A very painful sensation for the patient caused the removing process to be interrupted. The remaining adhesive was removed without pain or stinging to the still-sensitive skin by placing some 2,2,4,4,6,6,8,8-octamethylcyclotetrasiloxane on a cotton ball and gently rubbing the adhesive. The skin was not dried by this process and the patient could get dressed shortly thereafter without staining his clothes because the volatile methylsiloxane fluid had evaporated. The volatile methylsiloxane fluid used in this example is highly preferred because of its moderate volatility.

EXAMPLE 2

Adhesive bandages were easily removed from a patient's hairy limb, without the removal of hairs, by soaking the adhered bandages with the volatile methylsiloxane fluid described in Example 1 and stripping the bandage away from the limb.

EXAMPLE 3

Pressure-sensitive adhesive labels were removed from glass bottles by dabbing the label with a tissue saturated with the volatile methylsiloxane fluid described in Example 1. The adhesive was readily detackified, allowing the labels to be lifted from the glass bottles.

That which is claimed is:

1. A process for removing a pressure-sensitive adhesive from a substrate, said adhesive having tack, as measured by ASTM D2979-71, said process comprising applying a composition consisting essentially of a volatile methylsiloxane fluid to said adhesive and removing the thus-treated adhesive from said substrate, said volatile methylsiloxane fluid being sufficiently volatile to leave substantially no residue after 30 minutes at room temperature when 1 gram thereof is placed at the center of a No. 1 circular filter paper having a diameter of 185 mm. and being supported by its perimeter in an open room atmosphere.

2. A process for removing an article from a substrate, adhered thereto with a pressure-sensitive adhesive having tack, as measured by ASTM D2979-71, said process comprising applying a composition consisting essentially of a volatile methylsiloxane fluid to said adhesive and removing said article and its adhesive from said substrate, said volatile methylsiloxane fluid being sufficiently volatile to leave substantially no residue after 30 minutes at room temperature when 1 gram thereof is placed at the center of a No. 1 circular filter paper having a diameter of 185 mm. and being supported by its perimeter in an open room atmosphere.

3. A process according to claims 1 or 2 wherein the substrate comprises the human skin.

4. A process according to claims 1 or 2 wherein the volatile methylsiloxane fluid comprises a major amount of 2,2,4,4,6,6,8,8-octamethylcyclotetrasiloxane.

5. A process according to claim 3 wherein the volatile methylsiloxane fluid comprises a major amount of 2,2,4,4,6,6,8,8-octamethylcyclotetrasiloxane.

* * * * *